United States Patent
Ji et al.

(10) Patent No.: US 7,504,547 B2
(45) Date of Patent: Mar. 17, 2009

(54) METHOD OF PREPARING PERFLUOROALKADIENE

(75) Inventors: Hae-Seok Ji, Ulsal (KR); Ook-Jae Cho, Ulsan (KR); Jae-Gug Ryu, Ulsan (KR); Young-Hoon Ahn, Ulsan (KR); Bong-Suk Kim, Ulsan (KR); Dong-Hyun Kim, Ulsan (KR)

(73) Assignee: Foosung Co., Ltd., Kangnam-gu (KR)

( * ) Notice: Subject to any disclaimer, the term of this patent is extended or adjusted under 35 U.S.C. 154(b) by 0 days.

(21) Appl. No.: 11/797,355

(22) Filed: May 2, 2007

(65) Prior Publication Data

US 2008/0262195 A1 Oct. 23, 2008

(30) Foreign Application Priority Data

Apr. 20, 2007 (KR) .................. 10-2007-0038889

(51) Int. Cl.
*C07C 17/00* (2006.01)
*C07C 21/18* (2006.01)
(52) U.S. Cl. .................................... 570/156; 570/136
(58) Field of Classification Search ............. 570/136, 570/158, 156, 157
See application file for complete search history.

(56) References Cited

U.S. PATENT DOCUMENTS 2,668,182 A 2/1954 Miller
4,654,448 A * 3/1987 Bargigia et al. ............. 570/156
5,082,981 A * 1/1992 Bargigia et al. ............. 570/156
6,610,896 B2 * 8/2003 Miki et al. ................... 570/158
2002/0193643 A1* 12/2002 Miki et al. ................... 570/158

FOREIGN PATENT DOCUMENTS

| EP | 1247791 A1 * | 12/2002 |
| JP | 2001192346 A * | 7/2001 |
| JP | 2001192347 A * | 7/2001 |
| JP | 2004026800 A * | 2/2004 |

OTHER PUBLICATIONS

Hazeldine, R.N., "Fluoro-olefins. Part I. The Synthesis of Hexafluorobuta-1:3-diene", 1952, pp. 4423-4431.

* cited by examiner

*Primary Examiner*—Daniel M Sullivan
*Assistant Examiner*—Yate' K Cutliff
(74) *Attorney, Agent, or Firm*—Harness, Dickey & Pierce, P.L.C.

(57) ABSTRACT

Disclosed herein is a method of preparing a perfluoroalkadiene. A dihaloperfluorocarbon used as a starting material is added dropwise to a nonpolar organic solvent, a metal powder and an organic metal compound. The dihaloperfluorocarbon is slowly added dropwise in a temperature range from 30° C. to 150° C. for a certain period of time. Moreover, the nonpolar organic solvent used may be benzene, toluene, xylene, etc., and the organic metal compound is used by being dissolved in ethyl ether or tetrahydrofuran at a concentration of 1 to 3M. The metal powder used may be Mg, Zn, Cd, etc.

7 Claims, No Drawings

METHOD OF PREPARING PERFLUOROALKADIENE

CROSS-REFERENCE TO RELATED APPLICATION

This application claims under 35 U.S.C. §119(a) on Korean Patent Application No. 10-2007-0038889 filed on Apr. 20, 2007, the entire contents of which are incorporated herein by reference.

BACKGROUND OF THE INVENTION

1. Field of the Invention

The present invention relates to a method of preparing a perfluoroalkadiene and, more particularly, to a method of preparing a perfluoroalkadiene which can prevent side reactions at low cost.

2. Description of Related Art

Perfluoroalkadiene is a compound that can be used as a polymer for coating, an etching gas for semiconductor and a cleaning gas for semiconductor and has double bonds at both ends thereof.

Especially, in case of hexafluorobutadiene ($C_4F_6$) having double bonds at both ends thereof, there are a number of conventional methods.

Firstly, a method proposed by R. N. Haszeldine prepares $CCl_2F$—$CClF1$ by reacting $CCl_2F$=$CF_2$ with, I—Cl and then forms $CClF_2$—$CClF$—$CClF$—$CClF_2$ through a photoreaction in the presence of mercury. Subsequently, $CClF_2$—$CClF$—$CClF$—$CClF_2$ is processed with zinc in the presence alcohol such as ethanol to form $C_4F_6$ (J. Chem. Soc., 4423. 1952). However, this method causes several drawbacks in that it requires a number of processes and it causes environmental problems.

Secondly, a method proposed by W. T. Miller prepares $CF_2$=$CF$—$CClF$—$CClCF_2$ by reacting $CClF$=$CF_2$ (chlorotrifluoroethylene, CTFE) with itself at 550° C. and then forms $CF_2X$=$CFX$—$CClF$—$CCLCF_2$ (X=Br or I) through a chlorination or bromination reaction. Subsequently, $CF_2X$=$CFX$—$CClF$—$CClCF_2$ (X=Br or I) is processed with zinc to obtain $C_4F_6$ (U.S. Pat. No. 2,668,182). However, this method has also some drawbacks in that the yield of $CF_2$=$CF$—$CClF$—$CClF_2$ is low and it generates side reaction products in quantity.

Thirdly, there is a method proposed by G. Bargigia, et al., which can obtain $CF_2X$=$CFX$—$CClF$—$CClCF_2$ (X=Br or I) comparatively easily (U.S. Pat. Nos. 4,654,448 and 5,082,981); however, it still has drawbacks in that the handling of the compound is dangerous due to a high dehalogenation activity and its manufacturing cost is high since it uses an organic metal compound of high price.

The last method is disclosed in U.S. Patent Application No. 2002-193,643, in which $C_4F_6$ is prepared by adding dimethylformamide (DMF) to a solution in which a mixed solution of $CF_2I$—$CF_2$—$CF_2$—$CF_2I$, perfluoro solvent and zinc powder are heated to reflux. That is, the zinc powder and alkyl halide as an activator are mixed in a nonprotonic polar organic solvent such as DMF and a nonpolar organic solvent such as xylene, toluene, etc. Subsequently, $CF_2Br$—$CF_2$—$CF_2$—$CF_2Br$ is added to the mixed solution and then heated to reflux to obtain the $C_4F_6$.

The above-described four conventional methods commonly use polar organic solvents. If a polar organic solvent is used, side reaction products such as $CF_2H$—$CF_2$—$CF$=$CF_2$, $CF_2H$—$CF_2$—$CF_2$—$CF_2H$, and the like are generated more than about 10%, and the thus generated side reaction products exert a bad influence on the overall process yield. Moreover, since the zinc remaining after reaction is discharged in the form of sludge due to the polar organic solvent, it is difficult to dispose of the remaining zinc and to go through the following process. Furthermore, since it is difficult to recycle the used polar solvent, a high cost is required.

SUMMARY OF THE INVENTION

Accordingly, the present invention has been made in an effort to solve the above-described drawbacks, and an object of the present invention is to provide a method of preparing a perfluoroalkadiene using a nonpolar organic solvent.

In order to accomplish the above object, the present invention provides a method of preparing a perfluoroalkadiene by reacting a perfluorocarbon with a nonpolar organic solvent, an organic metal compound solution of 1 to 3M and a metal powder.

The organic metal compound is used as a reaction initiator in the reaction.

DETAILED DESCRIPTION OF THE INVENTION

Hereinafter, preferred embodiments in accordance with the present invention will be described in detail.

EXAMPLE

This Example relates to a method of preparing a perfluoroalkadiene having two double bonds at both ends thereof and the perfluoroalkadiene is represented by the following formula 1:

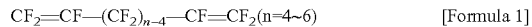

$$CF_2=CF—(CF_2)_{n-4}—CF=CF_2 (n=4\sim6) \quad \text{[Formula 1]}$$

A starting material for forming the perfluoroalkadiene of formula 1 is a dihaloperfluorocarbon. The dihaloperfluorocarbon is formed with a halogenation bond at both ends thereof and contains bromine (Br) or iodine (I). The dihaloperfluorocarbon is represented by the following formula 2:

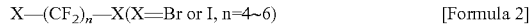

$$X—(CF_2)_n—X (X=Br \text{ or } I, n=4\sim6) \quad \text{[Formula 2]}$$

The dihaloperfluorocarbon is introduced to a nonpolar organic solvent containing an organic metal compound, e.g., a Grinard reagent, and heated to reflux to prepare the perfluoroalkadiene of formula 1.

In more detail, a dibromoperfluoroalkane or a diiodoperfluoroalkane that is a kind of dihaloperfluorocarbon is dissolved in a nonpolar organic solvent such as benzene, toluene, xylene, and the like, and a reaction initiator and a metal are introduced to remove BrF or IF, thus obtaining the perfluoroalkadiene.

The reaction initiator may be $C_2H_5MgX$ or $CH_3MgX$ (X=Br or I) contained in ethyl ether or tetrahydrofuran, and the introduced metal may be Mg, Zn, Cd, etc. Moreover, it is preferable that the reaction be carried out in a temperature range from 30° C. to 150° C.

Especially, as the reaction initiator that is an organic metal compound available industrially, $C_2H_5MgX$ or $CH_3MgX$ (X=Br or I) contained in ethyl ether or tetrahydrofuran at a concentration of 1 to 3M is used in 0.0005 to 0.05 equivalents per equivalent of the dihaloperfluorocarbon of formula 2 to initiate the reaction.

The metal used in the above reaction may be Mg, Zn, Cd, etc., and it is more effective to use the metal in the form of a powder (about 200 mesh). It is desirable in terms of efficiency and cost to use 1 to 5 equivalents per equivalent of the dihaloperfluorocarbon of formula 2.

The benzene, toluene and xylene mentioned above are just some examples of the nonpolar organic solvent and it is apparent to those skilled in the art that any nonpolar organic solvent would be suitable for use in the present invention. Moreover, it is preferable that the nonpolar organic solvent be added in a weight of 2 to 20 times the weight of the dihaloperfluorocarbon of formula 2.

Furthermore, air in the reactor in which the reaction is carried out should be purged by substituting with an inert gas and maintained in an anhydrous state. In addition, the reaction yield may be improved if a stirrer or a pump is used for stirring in the reaction.

After completion of the reaction, the metal is removed by a filtering process. The solvent may be recycled through a distillation process used in the art. The filtering process is desirably carried out by pressurizing the reactants for a rapid process.

It is preferable that the reaction be carried out in a temperature range from 30° C. to 150° C., and the reaction may be carried out in a temperature range from 60° C. to 120° C. in order to maximize the reaction efficiency and to inhibit side reactions.

Preparation Example 1

1 l of toluene, 1.5 equivalents of Mg powder and 50 ml of a 1M solution of $C_2H_5MgBr$ were placed in a 4-necked flask equipped with a reflux condenser connected to a cold trap cooled to a temperature lower than or equal to −40° C., a dropping funnel, and a mechanical stirrer rotating at more than 350 rpm under a nitrogen atmosphere. Subsequently, the mixed solution in the 4-necked flask was stirred at 350 rpm and heated to reflux. Then, 400 g of raw material of $CF_2Br$—$CF_2$—$CF_2$—$CF_2Br$ was added for 3 hours. The generated gas was collected in the cold trap cooled to below −40° C.

A total of 178 g of solution was collected in the cold trap about 1 hour after completing the addition of the raw material and the thus obtained solution was analyzed by gas chromatography analysis. As a result, 96% of $CF_2$=$CF$—$CF$=$CF_2$ (perfluorobutadiene), 2.2% of $CF_2H$—$CF_2$—$CF$=$CF_2$, 1.2% of $CF_2H$—$CF_2$—$CF_2$—$CF_2H$ and 1.0% of perfluorocyclobutene were identified and assayed as the components.

Preparation Example 2

1 l of toluene, 1.5 equivalents of Zn powder and 50 ml of 1M solution of $C_2H_5MgBr$ were placed in the same reactor used in Preparation Example 1 under a nitrogen atmosphere. Subsequently, the mixed solution was stirred by the mechanical stirrer at 350 rpm and heated to reflux. Then, 400 g of raw material of $CF_2Br$—$CF_2$—$CF_2$—$CF_2Br$ was added dropwise for 3 hours. A total of 155 g of solution was collected in the cold trap cooled to below −40° C. about 1 hour after completion of the dropwise addition and the thus obtained solution was analyzed by gas chromatography analysis. As a result, 94.5% of $CF_2$=$CF$—$CF$=$CF_2$ (perfluorobutadiene), 3.3% of $CF_2H$—$CF_2$—$CF$=$CF_2$, 1.2% of $CF_2H$—$CF_2$—$CF_2$—$CF_2H$ and 1.0% of perfluorocyclobutene were identified and assayed as the components.

Preparation Example 3

1 l of toluene, 1.5 equivalents of Zn powder and 50 ml of 1M solution of $CH_3MgBr$ were placed in the reactor of Preparation Example 1 under a nitrogen atmosphere. Subsequently, the mixed solution was stirred by the mechanical stirrer at 350 rpm and heated to reflux. Then, 400 g of raw material of $CF_2Br$—$CF_2$—$CF_2$—$CF_2Br$ was added dropwise for 3 hours. A total of 163 g of solution was collected in the cold trap cooled to below −40° C. and the thus obtained solution was analyzed by gas chromatography analysis. As a result, 97.3% of $CF_2$=$CF$—$CF$=$CF_2$ (perfluorobutadiene), 1.5% of $CF_2H$—$CF_2$—$CF$=$CF_2$, 0.8% of $CF_2H$—$CF_2$—$CF_2$—$CF_2H$ and 0.4% of perfluorocyclobutene were identified and assayed as the components.

Preparation Example 4

1 l of xylene, 1.5 equivalents of Cd powder and 50 ml of 1M solution of $CH_3MgBr$ were placed in the reactor of Preparation Example 1 under a nitrogen atmosphere. Subsequently, the mixed solution was stirred by the mechanical flask at 350 rpm and heated to reflux at a temperature 30 to 150° C. Then, 400 g of raw material of $CF_2BR$—$CF_2$—$CF_2$—$CF_2Br$ was added dropwise for 3 hours. A total of 158 g of solution was collected in the cold trap cooled to below −40° C. about 1 hour after completion of the dropwise addition and the thus obtained solution was analyzed by gas chromatography analysis. As a result, 95.7% of $CF_2$=$CF$—$CF$=$CF_2$ (perfluorobutadiene), 2.6% of $CF_2H$—$CF_2$—$CF$=$CF_2$, 1.2% of $CF_2H$—$CF_2$—$CF_2$—$CF_2H$ and 0.5% of perfluorocyclobutene were identified and assayed as the components.

Preparation Example 5

1 l of benzene, 1.5 equivalents of Zn powder and 100 ml of 1M solution of $C_2H_5MgBr$ were placed in the reactor of Preparation Example 1 under a nitrogen atmosphere. Subsequently, the mixed solution was stirred by the mechanical flask at 350 rpm and heated to reflux. Then, 400 g of raw material of $CF_2Br$—$CF_2$—$CF_2$—$CF_2Br$ was added dropwise for 3 hours. A total of 160 g of solution was collected in the cold trap cooled to below −40° C. about 1 hour after completion of the dropwise addition and the thus obtained solution was analyzed by gas chromatography analysis. As a result, 93.2% of $CF_2$=$CF$—$CF$=$CF_2$ (perfluorobutadiene), 3.4% of $CF_2H$—$CF_2$—$CF$=$CF_2$, 2.0% of $CF_2H$—$CF_2$—$CF_2$—$CF_2H$ and 1.4% of perfluorocyclobutene were identified and assayed as the components.

According to the above-described Preparation Examples, it is possible to prepare the target perfluoroalkadiene using a nonpolar organic solvent instead of a polar organic solvent. Accordingly, it is possible to easily separate the metal used in the reaction from the nonpolar organic solvent and recycle the solvent with a simple operation.

As described above, the perfluoroalkadiene is prepared by introducing an organic metal compound to a nonpolar organic solvent using a dihaloperfluorocarbon as a starting material. The preparation method in accordance with the present invention shows less than 3% of side reactions, while the conventional methods show more than 10% of side reactions. Moreover, with the use of the nonpolar organic solvent and the organic metal compound in a small quantity, the metal such as Mg, Zn, Cd, etc. is not discharged in the form of sludge after completion of the reaction. Accordingly, it is possible to easily separate the metal from the nonpolar organic solvent. Furthermore, since the nonpolar organic solvent can be recycled after completion of the reaction, it is possible to reduce the manufacturing cost.

As above, preferred embodiments of the present invention have been described and illustrated, however, the present invention is not limited thereto, rather, it should be understood that various modifications and variations of the present invention can be made thereto by those skilled in the art without departing from the spirit and the technical scope of the present invention as defined by the appended claims.

What is claimed is:

1. A method of preparing a perfluoroalkadiene of the following formula 1 by reacting a dihaloperfluorocarbon of the following formula 2 with a nonpolar organic solvent, an organic metal compound solution of 1M to 3M and a metal powder, wherein the nonpolar organic solvent is any one selected from the group consisting of toluene, xylene and benzene:

$CF_2=CF-(CF_2)_{n-4}-CF=CF_2 (n=4\sim6)$ [Formula 1]

$X-(CF_2)_n-X (X=Br\ or\ I, n=4\sim6)$ [Formula 2].

2. The method of claim 1, wherein the organic metal compound solution used as a reaction initiator is $C_2H_5MgX$ or $CH_3MgX$ (X=BR or I) contained in ethyl ether or tetrahydrofuran solvent, and the $C_2H_5MgX$ or $CH_3MgX$ (X=BR or I) is used in 0.0005 to 0.05 equivalents per equivalent of the dihaloperfluorocarbon of formula 2.

3. The method of claim 1, wherein the nonpolar organic solvent is used in a weight of 2 to 20 times the weight of the dihaloperfluorocarbon of formula 2.

4. The method of claim 1, wherein the metal powder is at least one selected from the group consisting of Mg, Zn and Cd.

5. The method of claim 1, wherein the metal powder is used in an amount of 1 to 5 equivalents per equivalent of the dihaloperfluorocarbon of formula 2.

6. The method of claim 1, wherein the reaction comprises:
   placing the nonpolar organic solvent, the metal powder and the organic metal compound solution in a reactor, and stirring and heating the mixture to reflux;
   adding the dihaloperfluorocarbon of formula 2 dropwise into the reactor; and
   collecting reaction products through a cold trap after completion of the dropwise addition.

7. The method of claim 6, wherein the dropwise addition of the dihaloperfluorocarbon of formula 2 is carried out in a temperature range from 30° C. to 150° C.

* * * * *